United States Patent [19]

Elstrom et al.

[11] Patent Number: 5,540,691
[45] Date of Patent: *Jul. 30, 1996

[54] OPTICAL DISTAL TARGETING METHOD FOR AN INTRAMEDULLARY NAIL

[76] Inventors: John A. Elstrom, 466 Illinois Rd., Lake Forest, Ill. 60045; Peter Elstrom, 31 28th St., San Francisco, Calif. 94110

[*] Notice: The term of this patent shall not extend beyond the expiration date of Pat. No. 5,417,688.

[21] Appl. No.: 444,961

[22] Filed: May 19, 1995

Related U.S. Application Data

[63] Continuation-in-part of Ser. No. 172,568, Dec. 22, 1993, Pat. No. 5,417,688.

[51] Int. Cl.⁶ .................................................. A61B 17/90
[52] U.S. Cl. ................... 606/64; 606/98; 606/96
[58] Field of Search .................. 606/96, 98, 97, 606/102, 104, 86, 53, 62, 64, 67, 68; 128/633, 634, 665, 664; 607/92, 93, 88

[56] References Cited

U.S. PATENT DOCUMENTS

| | | |
|---|---|---|
| 3,674,008 | 7/1972 | Johnson . |
| 4,050,450 | 9/1977 | Polanyi et al. ........................ 128/634 |
| 4,444,185 | 4/1984 | Shugar .................................. 128/634 |
| 4,621,628 | 11/1986 | Brudermann . |
| 4,646,743 | 3/1987 | Parris ....................................... 607/92 |
| 4,658,816 | 4/1987 | Ector, Jr. . |
| 4,667,664 | 5/1987 | Taylor et al. . |
| 4,776,340 | 10/1988 | Moran et al. ........................ 128/634 |
| 4,803,976 | 2/1989 | Frigg et al. .......................... 606/97 X |
| 4,817,591 | 4/1989 | Klaue . |
| 4,846,162 | 7/1989 | Moehring . |
| 4,865,025 | 9/1989 | Buzzi et al. .............................. 606/96 |
| 4,898,175 | 2/1990 | Noguchi ................................ 128/634 |
| 5,005,573 | 4/1991 | Bucharan ............................. 128/634 |
| 5,020,537 | 6/1991 | Gunther . |
| 5,036,853 | 8/1991 | Jeffcoat et al. ........................ 128/634 |
| 5,062,428 | 11/1991 | Charce .................................. 128/664 |
| 5,127,913 | 7/1992 | Thomas, Jr. . |
| 5,272,090 | 12/1993 | Gavish et al. ......................... 436/133 |
| 5,417,688 | 5/1995 | Elstrom et al. ........................... 606/64 |

FOREIGN PATENT DOCUMENTS

| | | |
|---|---|---|
| 2037266 | 7/1992 | Canada . |
| 3245680 | 11/1983 | Germany ................................ 606/98 |
| 9201422 | 2/1992 | WIPO ..................................... 606/98 |

OTHER PUBLICATIONS

Medoff, R. J.: Insertion of the Distal Screws in Interlocking Nail Fixation of Femoral Fractures, J. Bone and Joint Surg., 68–A:1275–1277, 1986.
Taylor, J. Charles: Fractures of the Lower Extremity in Campbell's Operative Orthopaedics, ED.B. Edited by A. H. Crenshaw, vol. 2, Interlocking Medullary (Russell–Taylor) Nailing, 1992, pp. 871–876.
Ordway, Craig B.: AIM Titanium Femoral Nail System Surgical Technique, Ace Medical Comany, pp. 1–8, 1991.
AIM Titanium Nail Surgical Technique, pp. 1–8, Ace Medical Company, 1991.
Wan et al.: Transmittance of Nonionizing Radiation in Human Tissues, J. Chemistry and Photobiology, vol. 34, pp. 679–681 (1981).

*Primary Examiner*—Guy V. Tucker
*Attorney, Agent, or Firm*—Banner & Allegretti, Ltd.

[57] ABSTRACT

Apparatus and methods for detecting the location of transverse holes of an intramedullary nail which has been inserted into a long bone and for aligning a surgical drill to the transverse holes. An insert having a light source at its distal end emitting non-ionizing electromagnetic radiation in the visible spectrum or infrared is inserted into the intramedullary nail, such that the light source is placed adjacent to the transverse holes. The light source may be a directional radiation output emitting the radiation in a direction perpendicular to the axis of the intramedullary nail. The light source may alternatively be an isotropic radiation output emitting radiation in all directions. The surgeon detects the transmitted radiation on the surface of the body of the patient and aligns the drill with the emitted radiation. Auxiliary video equipment, such as a camera and video monitor may be used to collect and display the emitted radiation, particularly if light in the infrared portion of the spectrum is used.

7 Claims, 5 Drawing Sheets

OPTICAL DISTAL TARGETING METHOD FOR AN INTRAMEDULLARY NAIL

This is a continuation-in-part of Ser. No. 08/172,568, filed Dec. 22, 1993, now U.S. Pat. No. 5,417,688.

BACKGROUND OF THE INVENTION

A. Field of the Invention

This invention relates generally to the field of surgery, and in particular relates to techniques for aligning a surgical drill with transverse holes of an intramedullary nail which has been implanted in long bones of a patient.

B. Description of Related Art

In repairing broken bones, and particularly long bones of the body such as the humerus, femur or tibia, a common surgical practice is to insert a hollow tubular part known as an intramedullary nail into the interior portion of the bone. The intramedullary nail is then secured in place with respect to the bone by installing one or more transversely-extending screws or bolts at the proximal and distal portions of the intramedullary nail. The intramedullary nail serves to enhance the healing of the broken bone by providing a rigid structure about which the broken portions of the bone may adhere.

In order to install the screws or bolts in the intramedullary nail and bone, a screw hole must be drilled transverse to the bone in direct alignment with each transverse hole in the intramedullary nail. This drilling is performed after the intramedullary nail has been inserted into the bone canal. It is desirable that drilling should pass cleanly through the transverse holes, to prevent metal shreds and shavings from being formed when the drill touches the nail. Such shavings may impede healing, and may cause post-operation discomfort or pain for the patient. Further, if the hole was not properly drilled, a second or even a third through hole may have to be drilled, weakening the bone and delaying the healing process. It is not possible to see the transverse holes directly, since the intramedullary nail is disposed inside the bone canal. An arrangement must be provided for the alignment of the surgical drill with the transverse hole s through the intramedullary nail.

Several approaches have been used to determine the location of the transverse holes to provide the necessary alignment of the drill with the hole during the drilling process. The approaches utilize conventional X-rays, in a majority of the time, or magnetic sources and sensor arrangements. The X-ray approach exposes the surgeon, the patient, and other personnel to a certain degree of irradiation for a relatively long period of time, which is a health concern. A recent approach to reduce long X-ray exposure during the procedure uses a laser light source coupled to an X-ray image intensifier. After alignment of the drill with the aid of an X-ray machine, the unit is turned off and a laser light spot is used to mark the location of the hole on the surface of the patient's extremity. The laser spot provides a starting location for drilling from the outside, but it does not provide visual alignment to the transverse hole inside the patient's extremity. Moreover, the surgeon's hand and drill get in the way of the laser.

The magnetic source and sensor approach provides a magnetic source or sensor inside and outside the patient and uses the magnetic field intensity as a function of position as the indicator of alignment. These magnetic source/sensor arrangements provide imprecise and cumbersome alignment either due to the magnetic source's relatively uniform maximum field strength in the region of maximum field, or the necessity of interpreting visual indicators providing the location of the magnetic sources and coordinating drilling movements with the indicators.

The use of magnets in aligning a surgical drill with the transverse holes of an intramedullary nail is described in the Thomas patent, U.S. Pat. No. 5,127,913. The problem of aligning an intramedullary nail with transverse anchoring members is also discussed in the patent to Klaue, U.S. Pat No. 4,817,591, the patent to Taylor, U.S. Pat. No. 4,667,664, the patent to Brudermann, U.S. No. Pat. No. 4,621,628, and Canadian Patent Application 2,073,266, entitled Distal Targeting System.

These efforts to solve the problem of accurate alignment of the surgical drill and the transverse holes of the intramedullary nail have achieved limited success, and only marginal acceptance by orthopedic surgeons. They also typically rely on expensive and cumbersome equipment. The methods that involve X-ray and image intensifier equipment also involve the display of bone and intramedullary nail images remote from the area of interest, such that the surgeon must look away from the patient to a screen to see if he or she is drilling in the proper location. This adds additional inconvenience to the surgeon. In actual practice, a free hand method of determining the location of the transverse holes is still often used, but this technique has its own inherent limitations and inaccuracies. Because of these shortcomings in the aforementioned techniques, the use of intramedullary nails as a treatment modality is much less frequent than it would otherwise be if a simple, safe, and accurate distal targeting technique were available to surgeons. The optical distal targeting system of the present invention overcomes these shortcomings of the prior art and provides a safe, relatively inexpensive, easy to use, and accurate means for locating transverse distal and proximal holes of an intramedullary nail.

SUMMARY OF THE INVENTION

Briefly, the present invention provides an apparatus for aligning a surgical drill with a distal transverse hole of an intramedullary nail. The intramedullary nail is insertable into a patient's bone and has a hollow body portion. The apparatus comprises, in combination, a light source emitting electromagnetic non-ionizing radiation in the visible or infrared portions of the spectrum, and an insert means for removably inserting the light source within the intramedullary nail such that the light source emits radiation from the distal transverse hole of the intramedullary nail. Suitable radiation collection and display equipment may by used to assist in the viewing of the emitted radiation on the surface of the patient. Alignment of the surgical drill to the radiation passing through said transverse hole of said intramedullary nail to the exterior surface of said patient aligns the surgical drill with the transverse holes, permitting accurate drilling of a hole though the bone and the transverse holes of the intramedullary nail. Preferably, the light source emits radiation having a wavelength of between about 550 nanometers and about 2.2 microns. Various different light source and insert constructions for use of in the invention are described. The invention may also be used for targeting of the proximal holes of the intramedullary nail.

BRIEF DESCRIPTION OF THE DRAWINGS

In the following detailed description of presently preferred embodiments of the invention, reference will be made to the accompanying drawings, wherein like numerals in the drawings refer to like elements in the various views, and wherein.

DETAILED DESCRIPTION OF THE PREFERRED EMBODIMENT

Figure 1:
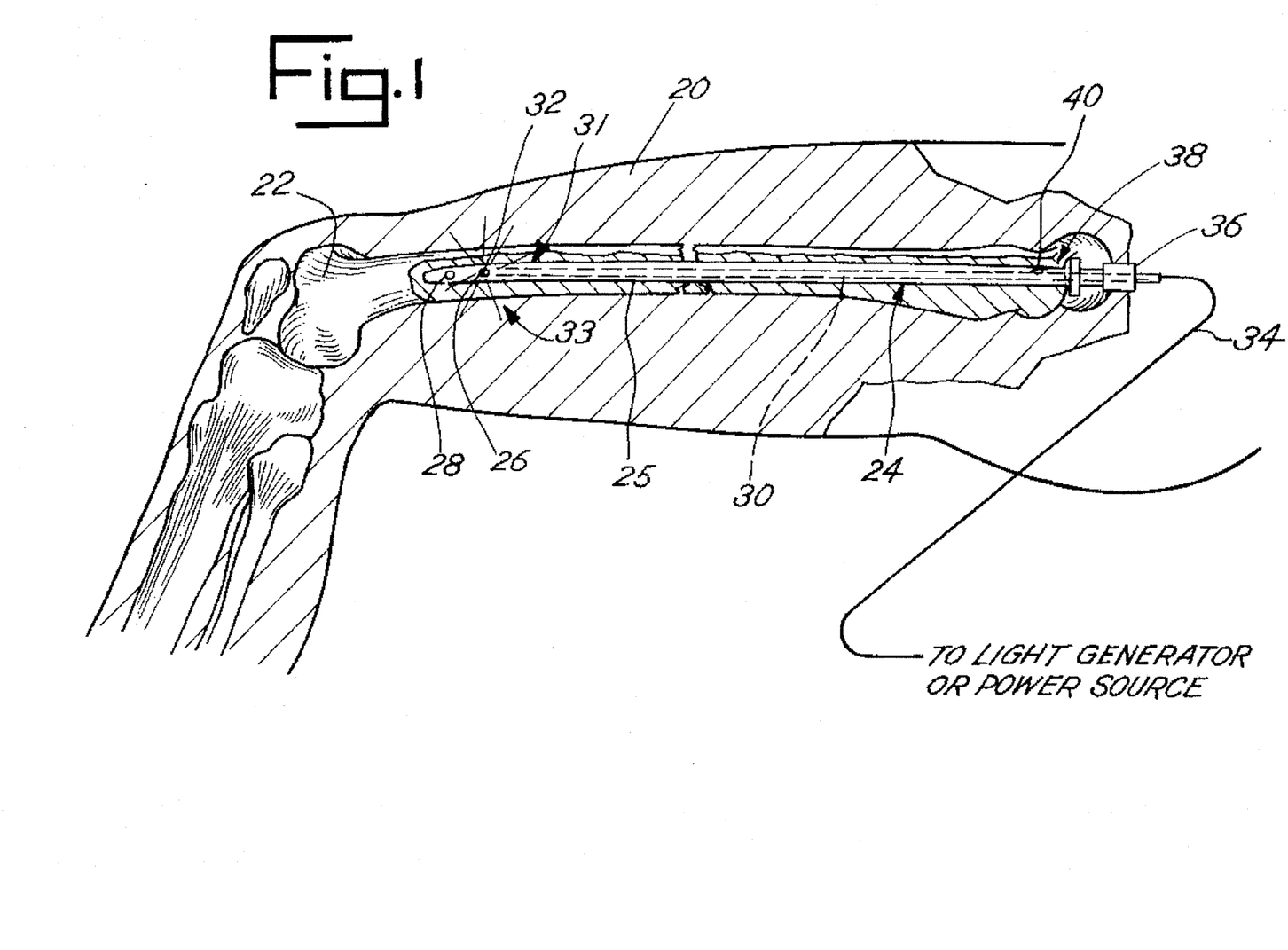
FIG. 1 is an illustration of the light source and insert of the present invention disposed within an intramedullary nail which has been inserted within a long bone of a patient.

In FIG. 1, a patient 20 having a broken long bone 22, for example, a broken femur, tibia, or humerus bone, is shown in which a conventional intramedullary nail 24 has been inserted into the interior region of the bone 22. The intramedullary nail 24 is an elongate metal rod having a hollow body portion 25 and a pair of transverse distal holes 26 and 28. The intramedullary nail 24 is secured to the bone 22 by means of screws or bolts (not shown in FIG. 1) which are installed transverse to the intramedullary nail 24 and which pass through the bone 22 and transverse distal holes 26 and 28 and proximal hole 40, thereby securing the bone 22 and intramedullary nail 24 to one another.

According to the present invention, an elongate insert 30 is inserted into the hollow body portion of the intramedullary nail 24. The insert 30 has a distal end or tip portion 31, and a light source 32 is mounted in the region of the distal end 31 of the insert 30. The light source 32 emits electromagnetic non-ionizing radiation 33, the wavelength being preferably between 400 nanometers and about 2 microns. It has been discovered that by inserting the light source having the foregoing characteristics within the intramedullary nail and adjusting the intensity of the light source, enough light is transmitted through the patient's body such that a surgeon can detect the emitted radiation on the surface of the patient 20 to thereby locate the location of the transverse holes 26 and 28 of the intramedullary nail. The radiation 33 is emitted through the transverse holes 26 and 28 and passes through the patient's body and is emitted from the surface of the patient 20. If the radiation 33 is of a wavelength longer than that of the visible spectrum, that is, above 760 nanometers, the surgeon wears infrared or night vision goggles or other equipment to perceive the radiation 33 passing through the transverse holes 26 and 28 to the surface of the patient 20. The phenomenon of transmittance of light through a human body is discussed in Wan et al., Transmittance of Nonionizing Radiation in Human Tissues, J. Chemistry and Photobiology, Vol. 34, pp. 679–681 (1981), which is incorporated by reference herein. The range of wavelengths which may be chosen for emission by the light source is a matter of choice and a function of the transmittance and absorption of the radiation by bodily tissues. Wavelengths in the visible or infrared portion of the spectrum are most suitable. A preferred range of wavelengths is between 500 nanometers and 2.2 microns. The visible wavelengths have the advantage of requiring no special viewing equipment to see the light passing through the transverse holes. The infrared wavelengths of course require the use of infrared or night vision goggles or infrared camera and display equipment, but such equipment works well in discriminating between the light source within the intramedullary nail and ambient light.

Referring again to FIG. 1, the light source 32 may be a fiber-optic output coupled to a fiber-optic cable 34, which in turn is led to a light source. Alternatively, the light source 32 may comprise a light emitting diode (LED), in which case a wire attached to the LED is led to a DC or AC power source. As discussed in more detail below, the light source 32 may comprise an isotropic radiation output, emitting radiation in all directions, or a directional radiation output, emitting radiation in one direction, or, alternatively, the light source 32 may comprise a pair of either isotropic radiation outputs or a pair of directional radiation outputs, or combination thereof. If a directional radiation output is chosen, the radiation should be oriented along an axis perpendicular to the axis of the intramedullary nail 24, to direct the radiation directly out of the transverse holes 26, 28. Pulsed light may also be employed. The pulsed light may assist the surgeon in distinguishing the emitted radiation 33 from ambient light.

Still referring to FIG. 1, the insert 30 may include a handle 36 for permitting easy insertion and retraction of the insert 30 from the intramedullary nail 24. When the surgeon has detected radiation 33 on the surface of the patient and drills through the patient's body 20 in alignment with the radiation 33 and the drill reaches the proximity of the transverse holes 26 or 28, the surgeon retracts the light source 32 and insert 30 from the intramedullary nail 24 by gripping the handle 36 and retracting the insert 30 from the nail 24 a few inches, to prevent the surgical drill from damaging the light source 32 or the insert 30. While the insert 30 and light source 32 are being retracted, the surgeon will still be able to locate the position of the transverse hole 26 or 28, especially if an isotropic radiation output is mounted at the end of the insert 30, because light reflects off the surface of the interior surface of the intramedullary nail 24 and passes outwardly through the transverse holes 26 or 28.

The proximal end 38 of the intramedullary nail 24 is also provided with a transverse proximal hole 40 for anchoring the proximal end 38 of the intramedullary nail to the bone 22. The insert may also be used to locate this hole precisely. Additional support brackets and other equipment which may be used in the insertion or manipulation of the intramedullary nail 24 during the surgical operation have been omitted from FIG. 1 in order to more clearly point out the features of the present invention. However, those of ordinary skill in the art will nevertheless recognize that such equipment may be used during insertion or manipulation of the intramedullary nail 24.

Figure 2:
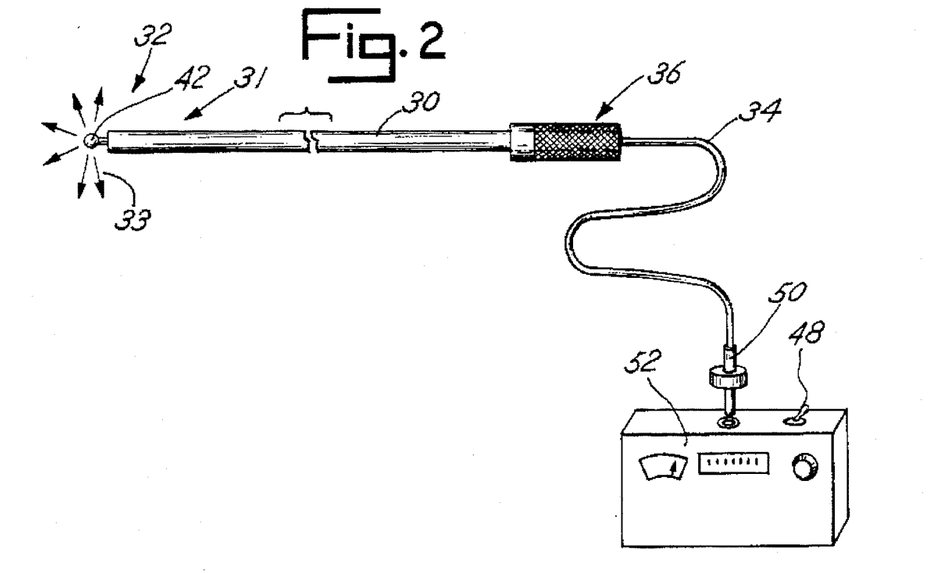
FIG. 2 is an illustration of insert and light source of FIG. 1, in which the insert is a tube encasing a fiber-optic cable and the light source comprises a fiber-optic isotropic radiation output.

Referring now to FIG. 2, the insert 30 and light source 32 of FIG. 1 is shown in an isolated view. The light source 32 of FIG. 2 comprises a isotropic radiation output 42 which emits radiation 33 in all directions. The insert 30 has a handle 36 having a gripping texture 46 applied to the surface of the handle 36. A fiber-optic cable 34 is led from the insert 30 to an SMA connector 50 which is in turned plugged into a light box 52. An on-off switch 48 is also provided which controls the illumination of the isotropic radiation output 42. The fiber-optic cable 34 runs down the interior portion of the insert 30 to the isotropic radiation output 42. The light box 52 will preferably have adjustments to adjust the wavelength of the radiation 33 emitted from the light source 32. The light box also preferably has adjustments to adjust the illumination intensity, power output, pulsation and other types of modulation of the radiation 33. For example, if infrared viewing goggles are used, the radiation can be modulated and tuned to settings in the goggles to enhance the detection of the radiation. It has been found that a power level in the range of 5 to 10 milliwatts is sufficient power in the region of the spectrum between 550 and 1,000 nanometers for ready detection of radiation on the surface of the patient 20. As transmittance of radiation through the human body as a function of wavelength in the region of the visible spectrum and infrared generally increases for longer wavelengths, if wavelengths of radiation 33 of between 400 and 760 nanometers are used, the absorption of the radiation in the body generally rises and higher power may be required. If radiation in the visible spectrum is desired for the radiation 33, the light can be filtered for a specific wavelength, for example, at 600 nanometers or 700 nanometers, to optimize against ambient light and to optimize perception of the light through the body. The filtering arrangement can be either at the generation of the light source, that is, light box 52, or preferably with binocular goggles attached to the head of the surgeon. The binocular goggles may also include magnification power if necessary. The head attachment of goggles frees the surgeon's hands to carry out the procedure without hinderance from any additional alignment mechanisms except for the surgical drill and scalpel.

A preferred light source is the Spectra Diodes Laboratories model SDL-2431-H2 laser diede with a fiber-optic output emitting radiation at a Wavelength of 800 nanometers. Infrared viewing goggles available from the Litton Electronics Devices Corp., 1215 S. 52nd Street, Tempe, Ariz. 85281, can be used for visually detecting the infrared radiation. Fiber-optic cables for use with the present invention are available from the Ensign-Bickford Optics Co., 150 Fisher Drive, P.O. Box 1260, Avon, Conn. 06001.

With the aid of the visual detection goggles and the adjustment of the optimal brightness for contrast by adjusting the controls of the light box 52, the surgeon proceeds to locate the transverse holes 26 and 28 inside the extremity of the patient 20. The targeting procedure consists of the direct placement of the drill over the illuminated holes perpendicular to the axis of the intramedullary nail and the subsequent drilling towards the inside of the extremity to the location of the nail. When the tip of the drill reaches a proximity of the nail, the insert 30 and light source 32 is withdrawn towards the proximal end of the intramedullary nail while continuing to illuminate near the transverse holes 28. Targeting proceeds with the drill penetrating through the transverse hole to the other side of the extremity. The procedure is repeated for the second transverse hole 26 if necessary. Once distal targeting is complete, the illumination system (insert 30 and light source 32) is removed from the nail. The illumination system is reusable after performing the necessary sterilization procedures.

Figure 3:
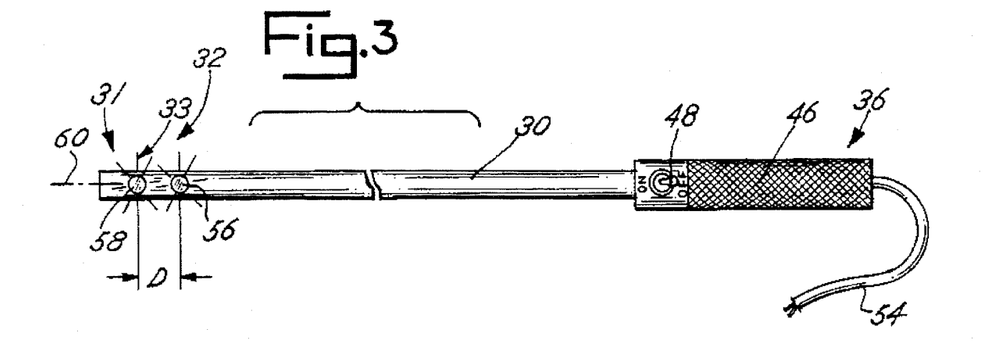
FIG. 3 is an illustration of an alternative embodiment of the invention wherein the light source comprises a pair of light emitting diodes having a directional radiation output perpendicular to the long axis of the insert.

Referring now to FIG. 3, an alternative embodiment of the invention is shown in which the light source 32 comprises a pair of LEDs 56 and 58 which emit radiation perpendicular to the axis 60 of the insert 30. The LEDs are mounted in a fashion perpendicular to the long axis 60 of the insert 30 such that the spacing D between the LEDs is substantially equal to the distance between the centers of the two distal transverse holes 26 and 28 of the intramedullary nail 24 (FIG. 1). Thus, when the insert 30 is fully inserted into the intramedullary nail 24, the diodes 58 and 56 are placed directly at the center of the distal transverse holes 28 and 26, respectively, of the intramedullary nail 24. Once inserted into the intramedullary nail 24, the insert 30 is manipulated by rotating the handle 36 until the radiation 33 passes directly out of the intramedullary nail through the holes 26 and 28. In the embodiment of FIG. 3, wires 54 are passed through the insert 30 to the LEDs 56 and 58 to supply a DC voltage to the LEDs 56 and 58. Suitable LEDs for use with the present invention may be purchased from the Hamamatsu Corp., 360 Foot Hill Road, P.O. Box 6910, Bridgewater, N.J. 08807-0910. The LEDs 56 and 58 of FIG. 3 may be the directional radiation outputs as shown, or may be isotropic radiation outputs similar to that shown in FIG. 2. Alternatively, only one LED may be provided in the distal portion 31 of the insert 30. The wavelength of radiation 33 emitted by diodes 56 and 58 may also vary. However, wavelengths of between 600 and 1,000 nanometers are preferred. LEDs are available from the Hamamatsu Corp. which emit radiation in this region of the spectrum. Another alternative configuration has an isotropic LED located at the distal tip of the insert 30 in a parallel fashion relative to the axis 60 exactly like the fiber-optic output 42 of FIG. 2.

Figure 4:
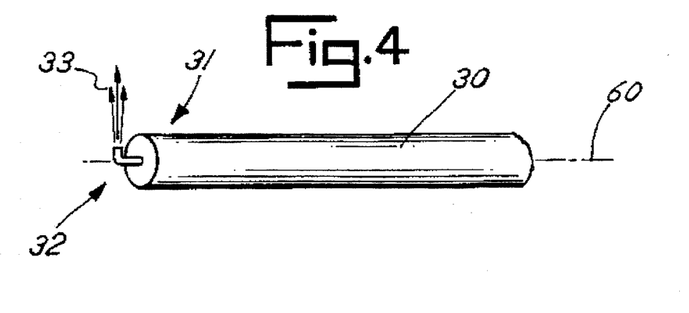
FIG. 4 is an alternative embodiment of the insert and light source of FIG. 2, in which the light source comprises a directional radiation output emitting light in an orientation perpendicular to the axis of the insert.

Referring now to FIG. 4, the insert 30 may alternatively have a light source 32 comprising a fiber-optic directional radiation output which emits radiation 33 perpendicular to the axis 60 of the insert 30. A suitable directional radiation output for a fiber-optic cable is sold by Cuda Products Co.

Figure 5:
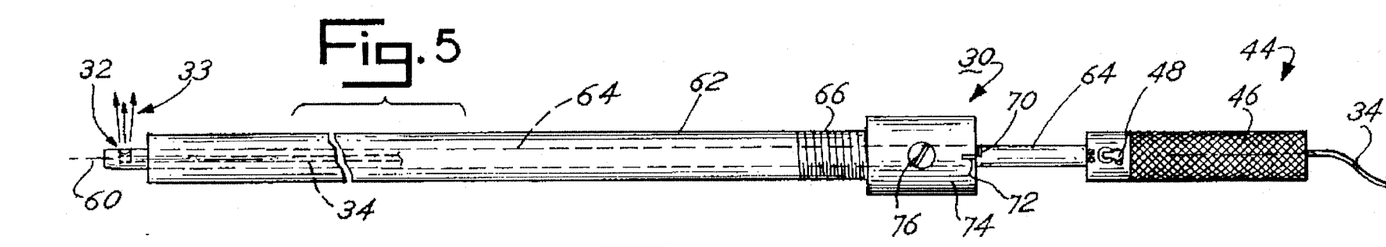
FIG. 5 is an alternative embodiment of the invention in which the insert comprises an outer insert member and an inner member, and wherein the light source comprises a directional radiation output.

Referring now to FIG. 5, an alternative embodiment of the invention is shown in which an outer insert 62 and an inner insert 64 are provided in which the inner insert 64 carries a fiber-optic cable 34 and a light source 32 which emits radiation 33. The outer insert 62 is an elongate hollow cylindrical housing which serves to protect the inner insert 64 and light source 32 when the inner insert 64 is inserted into the intramedullary nail. The outer insert 62 has a threaded region 66 for threading the outer insert 62 onto the intramedullary nail 24, or to a handle which is mounted to the proximal end of the intramedullary nail 24. Outer insert 62 is preferably made of a semi-rigid sterilizeable material. A thin hollow plastic or metal tube made from polysulfone, stainless steel, or vitalium, may be satisfactory. The inner insert 64 may also be composed of a semi-rigid or rigid plastic or metal material, such as stainless steel or any other suitable sterilizeable material. The inner insert 64 encases the fiber-optic cable 34 or electrical wires for the light output. The inner insert 64 is reciprocable relative to the outer insert 62. When the outer insert 62 is inserted into the intramedullary nail 24, the inner insert 64 is inserted within the outer insert 62 into position such that the light source 32 is at the transverse hole 26 or 28 of the intramedullary nail 24.

The inner insert 64 has an alignment marking 70 which, when positioned adjacent to the alignment mark 72 on the handle 74 of the outer insert 62, indicates that the light source 32 is positioned directly at the transverse hole 26 or 28 of the intramedullary nail. A screw 76 is provided on the handle 74 such that when the alignment mark is in the proper position, the screw 76 is tightened to fix the position of the inner insert 64 relative to the outer insert 62. The inner insert 64 may be provided with two alignment marks 70 which are spaced a distance apart which is equal to the separation distance of the centers of the two holes 26 and 28 of the intramedullary nail 24. Thus, the surgeon will align the two alignment marks 70 relative to the alignment mark 72 to place the light source 32 directly at each of the transverse holes 26 and 28.

Figures 6, 7, 8, 9:
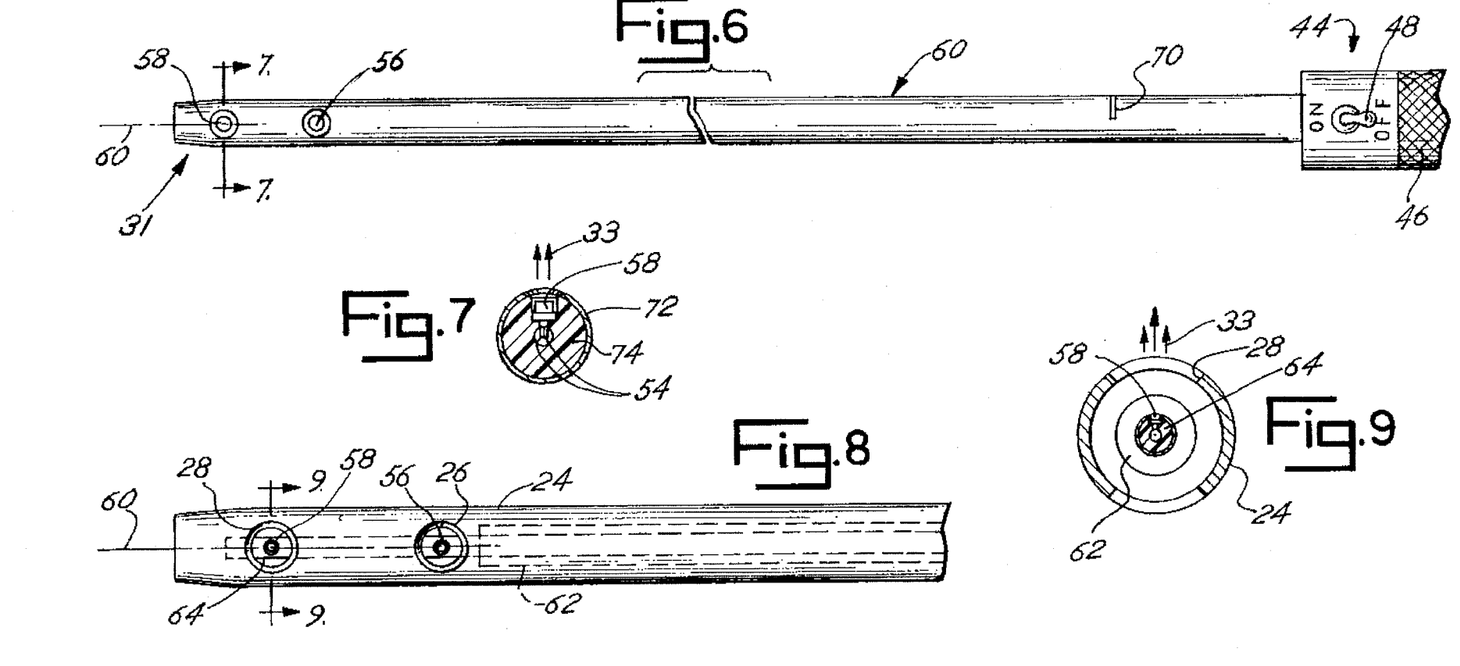
FIG. 6 is a plan view of the inner insert member of FIG. 5.
FIG. 7 is a cross-sectional view of the inner inert of FIGS. 5 and 6 along the lines 7—7 of FIG. 6.
FIG. 8 is a plan view of the insert and light source of FIG. 3 installed within an intramedullary nail.
FIG. 9 is a cross-sectional view of the intramedullary nail and insert of FIG. 8 along the lines 9—9 of FIG. 8.

Referring now to FIG. 6, an alternative form of the inner insert 64 of FIG. 5 is shown isolated from the outer insert 62. The inner insert 64 has a pair of LEDs 56, 58 mounted in the distal portion 31 of the inner insert 64. The LEDs 56 and 58 of FIG. 6 are preferably directional radiation outputs which emit radiation perpendicular to the long axis 60 of the inner insert 154. The inner insert 64 of FIG. 6 is shown in a cross-sectional view in FIG. 7 along the lines 7—7 of FIG. 6. The inner insert 64 has a stainless steel (or other suitable material) sheath 72 housing a plastic or other suitable material 74 in which the diode 58 is embedded. Wires 54 are provided within the inner insert 64 to apply DC voltages to LEDs 56, 58.

Referring now to FIG. 8, the inner insert 64 of FIG. 6 is shown inserted within an intramedullary nail 24. The outer insert 62 has been inserted into the intramedullary nail 24, and the threaded portion 66 (FIG. 5) of the outer insert 62 has been fixed onto the proximal end of the intramedullary nail. The inner insert 64 has been inserted into the outer insert 62 until the alignment mark 70 (FIG. 6) has aligned with the alignment mark 72 on the handle 74 of the outer insert 62. The LEDs 56 and 58 are then placed directly at the transverse holes 26 and 28 of the intramedullary nail 24. The arrangement of FIG. 8 is shown in a cross-sectional view in FIG. 9 along the lines 9—9 of FIG. 8.

Figure 10:
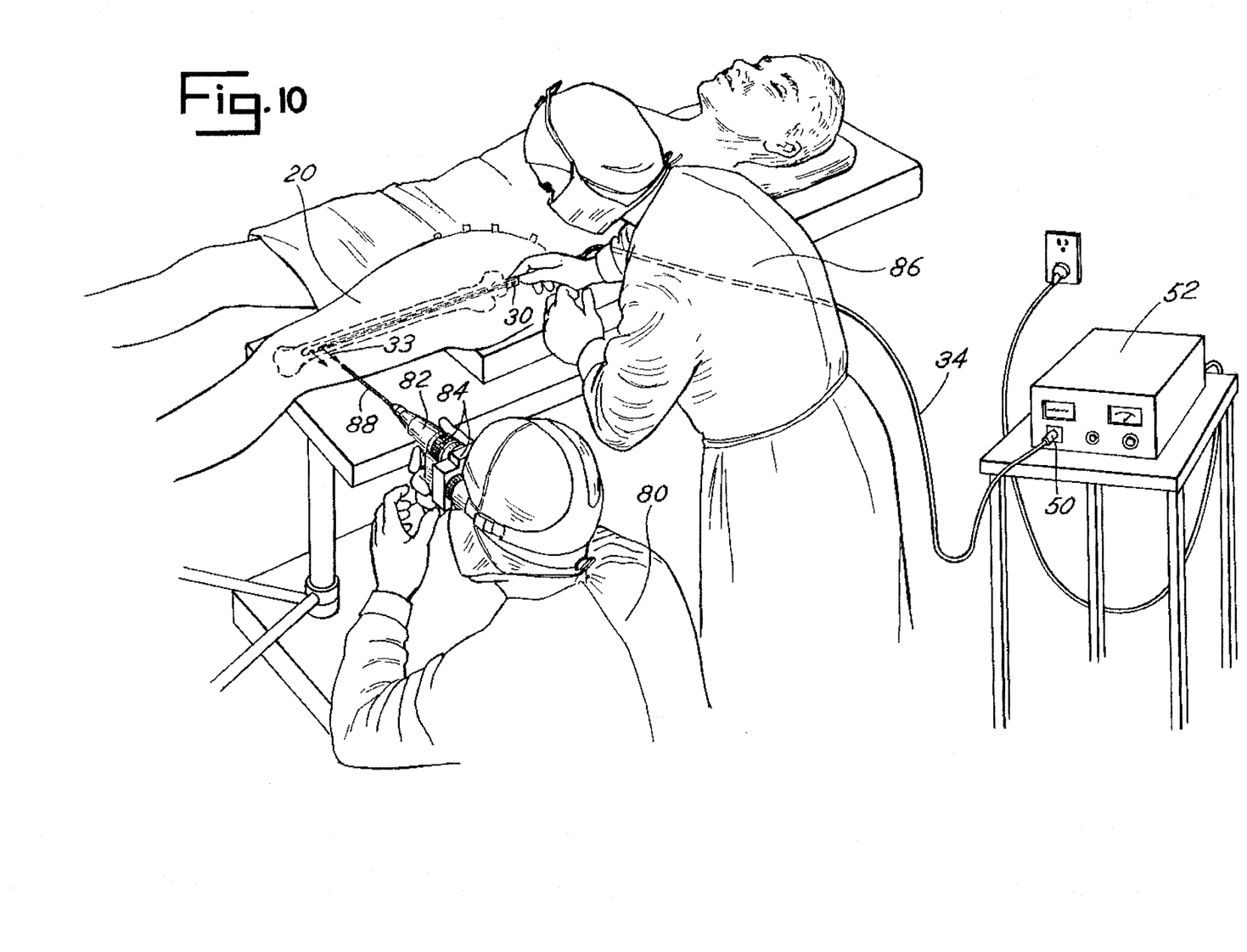
FIG. 10 is an illustration of a surgeon and an assistant aligning the surgical drill with radiation passing through the transverse holes of the intramedullary nail to the exterior surface of the patient to thereby align the surgical drill with the transverse holes.

A representative example of how the invention is used in illustrated in FIG. 10. A surgeon 80 uses a surgical drill 82 during surgery on the patient 20 having a broken femur. An insert 30 having a light source (not shown) has been inserted such that two directional radiation outputs are placed directly below the two transverse holes 26 and 28 of the intramedullary nail 24, emitting radiation at 800 nanometers. In this representative example, the insert 30 carries a fiber-optic cable 34 which is plugged into a light source 52 by means of an SMA plug 50. Surgeon 80 is wearing an infrared detection goggle arrangement 84 such as the Litton model M982 high performance goggle. However, other suitable equipment may be used to display the location of the radiation, particularly if the wavelength of the radiation is not in the visible spectrum (such as a video monitor/TV screen). The surgeon orients the surgical drill 82 in alignment with radiation 33 observed on the surface of the patient's body 20.

Figure 11:
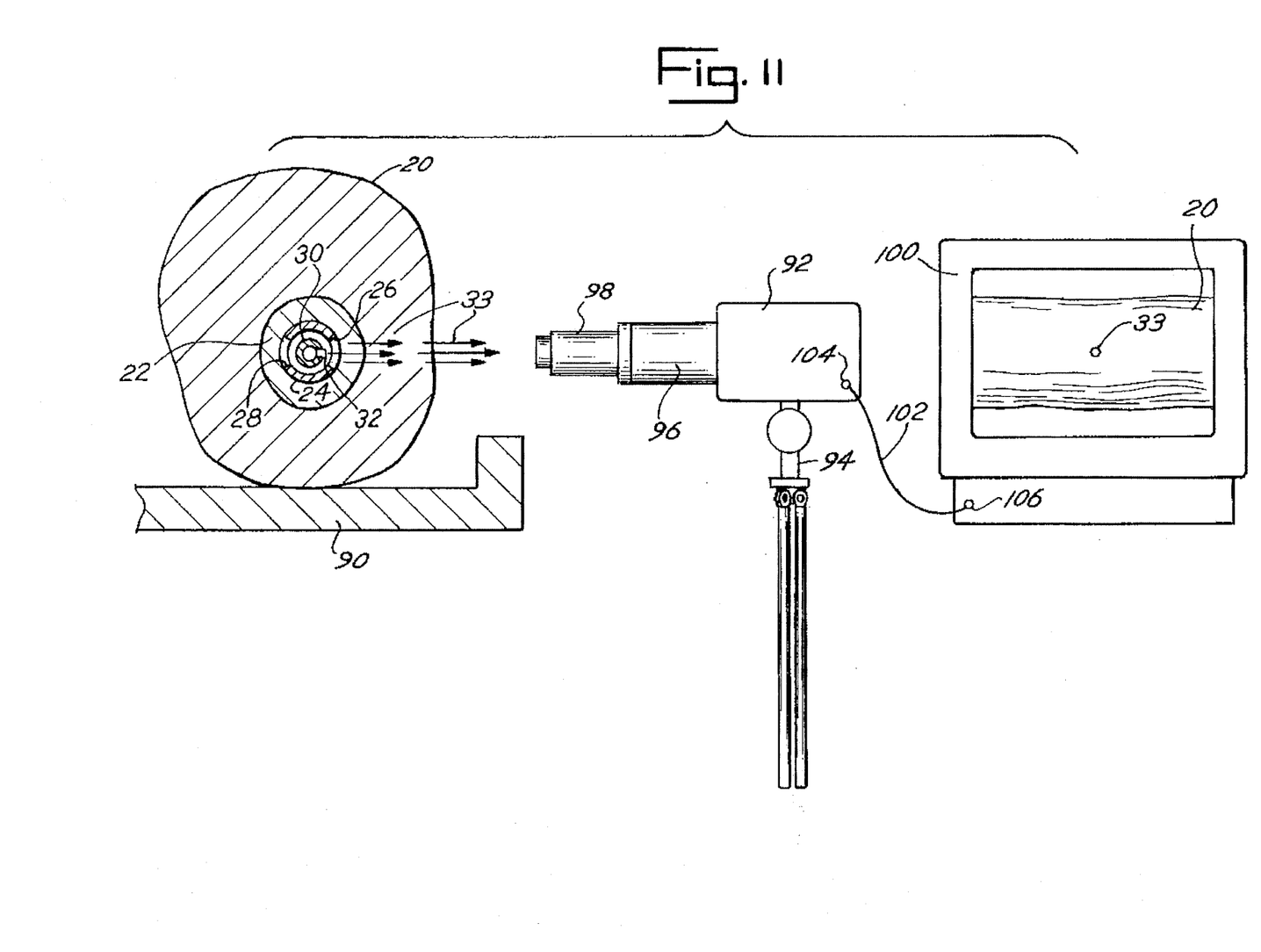
FIG. 11 is an illustration of the use of a camera and video monitor to assist the surgeon in detecting the radiation emitted from the light source.

In order to visually observe the radiation from a light source 32 with the aid of a video monitor such as a TV screen, a video camera, such as a Charge-Coupled Device (CCD) camera, is needed to collect the emitted radiation. Referring to FIG. 11, a representative CCD camera such as a Sony™ home video camera 92 is shown mounted on a tripod 94 with its legs in a folded condition so as to take up as little amount of space in the operating room as possible. The camera 92 is placed adjacent to the operating table 90, with the patient 20 placed thereon, and oriented such that it collects the radiation 33 emitted from the skin of the patient 20. The light source 32, attached to insert 30, is placed within the intramedullary nail 24 adjacent to the transverse holes 26 and 28.

The CCD camera 92 has a Video Output terminal 104 that is coupled via co-axial cable 102 to the Video Input terminal 106 of the TV screen 100. The image of the patient 20 and the emitted radiation 33 is displayed on the TV screen. In cases where the CCD camera 92 cannot detect the radiation 33 due to the spectral sensitivity limits of the camera, radiation collection and amplification equipment can be used. For example, an infrared viewing device such as a night vision monocular 98 (such as Litton Model M983, part no. 240008-001) is coupled to a camera 92 fitted with a removable objective lens by first removing the lens, then attaching a camera relay lens 96 (such as Litton part no. 206812-100) having a C-mount, and then mounting the monocular 98 to the camera relay lens 96. The monocular 98 serves as the collector and amplifier of the emitted radiation, and permits the camera to process the radiation. The camera 92 generates a video signal that is displayed on the TV screen 100. It will be readily appreciated that other types of collecting and amplifying devices, such as a photo-multiplier tube attached to the input lens of the camera, can be used. Other suitable apparatus having the electronics to collect the radiation and process the collected radiation into a video signal for display can be used. The scope of the present invention is intended to encompass the use of all such equipment.

Further, when a light source is used in which the emitted radiation is in the region of 1000 nm to 2 microns or thereabouts, an infrared camera is generally needed to collect the emitted radiation. The collected radiation can then be processed and transmitted in the form of an image to be displayed on a TV screen. Presently preferred infrared cameras and viewers are the 1800 nm or 2200 nm devices sold under the trademark Find-R-Scope, part nos. 85400 and 85353, available from FJW Optical Systems, Inc. 629 S. Vermont St., Palatine, Ill. 60067. These units can be easily mounted on a standard tripod and appropriately positioned with respect to the surgeon and patient in order to collect and record the emitted radiation. Co-axial cables connect the video output of the camera to the video input of the TV monitor. Other infrared cameras and infrared goggles suitable for viewing the emitted radiation in accordance with the present invention are available from Hamamatsu of Wakefield, Mass. and ITT of Roanoke, Va.

Referring again to FIG. 10, when the surgeon 80 is ready to perform the distal targeting procedure, the assistant 86 inserts the insert 30 within the intramedullary nail. The assistant 86 then dims the lights in the operating room (if necessary) and turns the light source on, causing radiation to emit from the light source. The assistant may make suitable adjustments to the light box, such as increasing or decreasing the power, changing the wavelength, or modulating the radiation. An assistant positions the camera 92 (if one is being used in the procedure) adjacent the patient and slightly to one side so as not to interfere with the drilling of the hole through the intramedullary nail. The surgeon 80 or the assistant 86 visually detects the radiation 33 on the surface of the patient 20, or on the TV screen 100 (FIG. 11). The surgeon 80 may move the insert 30 back and forth until the maximum amount of light is detected on the surface of the body 20 to ensure that the light source is placed directly at the transverse holes of the intramedullary nail. When the surgeon is confident that the light source is placed directly at the transverse holes of the intramedullary nail, the surgeon 80 aligns the surgical drill 82 with the radiation 33 passing through the transverse holes of the intramedullary nail, which permits accurate drilling of a hole through the patient's body 20, the bone, and through the intramedullary nail without shaving or otherwise disturbing the intramedullary nail 24. Moreover, because the distal targeting has been accurately performed there is no need to redrill unnecessary holes due to misalignment of the drill and the transverse holes. As noted earlier, when the drill tip 88 reaches the vicinity of the intramedullary nail, the insert 30 is withdrawn from the intramedullary nail slightly so that the drill tip 88 does not damage the insert or the light source. Once the distal targeting and drilling procedure has been completed, the insert 30 is completely withdrawn from the intramedullary nail and sterilized before reuse.

The insert and light source of the invention can also be used for locating the proximal hole 40 of the intramedullary nail 24 (FIG. 1). The surgeon simply inserts the insert only part way into the intramedullary nail until the light source is located at the proximal hole 40. The detection and alignment of the surgical drill proceeds as described above. The surgeon may also use a special insert of relatively short length specifically adapted for use in locating the proximal hole 40. The only difference in construction and operation of such a special insert from those previously described herein is that the length of insert is less, due to the relatively short distance from the proximal hole 40 the proximal end of the intramedullary nail.

While the foregoing specification has described presently preferred embodiments of the invention, it will be appreciated that many modifications and variations may be made to the apparatus and techniques discussed herein without departure from the true spirit and scope of the invention. Other types of light sources may be inserted within the intramedullary nail, such as phosphor dyes which are excited to emit radiation. The phosphor dye is activated by any well known method prior to insertion into the intramedullary nail, such as by exposing the dye to ultraviolet radiation, introducing reagents into the dye, agitating the dye, or whatever other types of activation procedures are required depending on the type of dye being used. The wavelengths of radiation may include the visible portion of the spectrum and the infrared, up to 2 microns or thereabouts. Other types of insert constructions and alignment mechanisms may be used without departure from the spirit of the invention. Further, the invention contemplates that other radiation collection and display equipment other than that described above may be used. This true spirit and scope of the invention is defined by the claims, interpreted in light of the specification.

We claim:

1. A method of aligning a surgical drill with a transverse hole of an intramedullary nail, said intramedullary nail insertable into a patient's bone and having a hollow body portion, comprising the steps of:

a) inserting a source of nonionizing electromagnetic radiation within said hollow body portion of said intramedullary nail such that said radiation passes through said transverse hole of said intramedullary nail;

b) visually detecting said radiation emitted through said transverse hole on the exterior surface of said patient, said step of visually detecting said radiation comprising the step of collecting said emitted radiation, generating a video signal of said radiation, and displaying said video signal; and c) aligning said surgical drill with said detected radiation.

2. The method of claim 1, wherein said radiation is in the infrared portion of the spectrum.

3. The method of claim 2, wherein said radiation has a frequency of between 1000 nm and about 2.2 microns.

4. The method of claim 1, wherein said radiation is collected by a camera, and wherein said camera further comprises a radiation collection and amplification device.

5. The method of claim 4, wherein said radiation collection and amplification device comprises an infrared viewing device.

6. The method of claim 1, wherein said radiation is collected by a charge-coupled device.

7. The method of claim 1, wherein said radiation is displayed on a video monitor.

* * * * *